United States Patent [19]

McIntosh

[11] Patent Number: 5,405,770
[45] Date of Patent: Apr. 11, 1995

[54] HELIOTHIS SUBFLEXA CELL LINE FOR THE PRODUCTION OF BACULOVIRUSES

[75] Inventor: Arthur H. McIntosh, Columbia, Mo.

[73] Assignee: The United States of America as represented by the Secretary of Agriculture, Washington, D.C.

[21] Appl. No.: 6,400

[22] Filed: Jan. 21, 1993

[51] Int. Cl.⁶ .................. C12N 7/04; C12N 7/08; C12N 5/02
[52] U.S. Cl. .................. 435/235.1; 435/236; 435/239; 435/240.2; 435/240.21; 435/240.25
[58] Field of Search ............. 435/235.1, 240.2, 240.21, 435/240.25, 236, 239

[56] References Cited

U.S. PATENT DOCUMENTS

| | | | |
|---|---|---|---|
| 4,870,023 | 9/1989 | Fraser et al. | 435/320.1 |
| 4,911,913 | 8/1990 | Hostetter et al. | 424/93 R |
| 5,024,947 | 6/1991 | Inlow et al. | 435/240.31 |
| 5,041,379 | 8/1991 | Fraser et al. | 435/235.1 |
| 5,169,784 | 12/1992 | Summers et al. | 435/320.1 |

OTHER PUBLICATIONS

McIntosh, Arthur H., et al., "Replication of *Autographa Californica* Nuclear Polyhedrosis Virus in Five Lepidopteran Cell Lines", *Journal of Invertebrate Pathology*, 54, pp. 97–102, 1989.

McIntosh, Arthur H., "In Vitro Infectivity of a Clonal Isolate of *Syngrapha falcifera* (Celery Looper) Multiple Nuclear Polyhedrosis Virus", *Journal of Invertebrate Pathology*, 57, pp. 441–442, 1991.

*Primary Examiner*—Douglas W. Robinson
*Assistant Examiner*—L. Blaine Lankford
*Attorney, Agent, or Firm*—M. Howard Silverstein; Randall E. Deck; John D. Fado

[57] ABSTRACT

A cell line obtained from *Heliothis subflexa*, designated BCIRL-HS-AM1, and an in vitro process using the cell line to produce viral agents including viruses, viral particles, and/or occlusion bodies. The cell line is particularly useful in the production of baculoviruses and occlusion bodies of baculoviruses.

7 Claims, No Drawings

HELIOTHIS SUBFLEXA CELL LINE FOR THE PRODUCTION OF BACULOVIRUSES

BACKGROUND OF THE INVENTION

1. Field of the Invention

The invention relates to a cell line obtained from *Heliothis subflexa*, designated BCIRL-HS-AM1, and a process of producing viral agents such as viruses, viral particles, and/or inclusion bodies in vitro. The cell line finds particular utility in the production of baculoviruses, and especially occlusion bodies (OB) of the baculoviruses *Anagrapha (Syngrapha) falcifera* multiple nuclear polyhedrosis virus (AfMNPV) and *Autograph californica* multiple nuclear polyhedrosis virus (AcMNPV).

2. Description of the Prior Art

Baculoviruses are valuable as biological control agents for Lepidopteran pests. The viruses are currently mass-produced in vivo in insect larvae under nonaseptic conditions. The process is difficult to control and the viruses thus produced are subject to contamination. Further, the process is labor-intensive requiring the continuous supply of insect larvae in which the viruses are produced.

*Autographa californica* multiple nuclear polyhedrosis virus is well recognized for its use as a potential biocontrol agent because of its wide host range within the order Lepidoptera. *Anagrapha falcifera* multiple nuclear polyhedrosis virus is a baculovirus recently isolated from a celery looper and differs from AcMNPV both in its REN pattern and its greater infectivity for *Helicoverpa zea* larvae. AfMNPV is equally infectious for both *H. zea* and *H. virescens* larvae and possesses a wide range infecting over 30 species from 10 families in the order Lepidoptera.

Insect cell lines have been established from major Lepidopteran pests of agriculture and forestry [Hink et al., Invertebrate Cell Culture Media and Cell Lines In "Techniques in Setting Up and Maintenance of Tissue and Cell Cultures", E. Kurstak, ed., Elsevier, N.Y. pp. 1–30 (1985)]. These cell lines and techniques have been identified as the future source of mass-produced viral insecticides. Before cell technology can be a viable alternative to in vivo production of insecticides, however, the conditions for in vitro production must be systematically evaluated and optimized [McIntosh et al., J. Kansas Entomol. Soc. 55: 354–386 (1982)].

SUMMARY OF THE INVENTION

We have discovered a cell line from *Heliothis subflexa*, which has been designated BCIRL-HS-AM1, and a process using the cell line for producing viral agents. The cell line is particularly useful in the production of baculoviruses and especially the baculoviruses *Anagrapha falcifera* multiple nuclear polyhedrosis virus (AfMNPV) and *Autographa californica* nuclear polyhedrosis virus (AcMNPV), unexpectedly producing substantially higher yields of virus than other Lepidopteran cell lines.

Production of the viruses and baculoviruses in the cell line is accomplished using cell culture techniques well known in the art. Cells of the *Heliothis subflexa* cell line, BCIRL-HS-AM1, are provided in a culture medium in vitro, inoculated with virus, and incubated. The viral agents produced are subsequently collected.

The primary objective of this invention is to provide a cell line and method of using the same to mass-produce viral agents or mixtures thereof in vitro. In the preferred embodiment, the cell line is used in the production of baculoviruses, especially OB of the baculoviruses AfMNPV and AcMNPV. The viruses, viral particles, and/or occlusion bodies produced by this invention may be employed as biological control agents for Lepidopteran pests.

Another objective of this invention is to provide a cell line for replicating genetically engineered baculoviruses which express foreign proteins of medical, pharmaceutical, and veterinary importance.

Yet another objective of this invention is to provide a cell line which may be cloned and frozen in liquid nitrogen. The production of baculoviruses using the cell line may be performed in a clean, controllable environment free from microbial contamination.

Other objects and advantages of this invention will become readily apparent from the ensuing description.

DETAILED DESCRIPTION OF THE INVENTION

The cell line of the invention was obtained from ovarian tissue taken from female pupae of *Heliothis subflexa*, and was designated BCIRL-HS-AM1. Generally, the ovarian tissue was aseptically removed from 7 female pupae of *H. subflexa*, minced, trypsinized and grown in primary culture (in TC199-MK medium). After repeated passage, the cells of the BCIRL-HS-AM1 cell line were eventually obtained from the mixed cell populations in pure or substantially pure form.

In vitro mass-production of viral agents may now be accomplished using the cell line of the invention. The term viral agent is defined herein to include viruses, viral particles, and occlusion bodies, as well as mixtures thereof (e.g. viruses and occlusion bodies). Without being limited thereto, the cell line may be used to produce the virus and OB of baculoviruses, particularly AfMNPV (previously named *Syngrapha falcifera* multiple nuclear polyhedrosis virus, SfMNPV) and AcMNPV. However, it is understood that other viruses or baculoviruses may be produced.

Production of the viruses using the cell line of this invention may be accomplished using conventional techniques, such as described by McIntosh and Ignoffo [J. Invertebrate Pathology, 54: 97–102, (1989), the contents of which are incorporated by reference herein]. In accordance with this method, cells of the *Heliothis subflexa* cell line, BCIRL-HS-AM1, are provided in a culture medium in vitro, and are inoculated with virus or baculovirus. The cell culture is then incubated a sufficient time and under conditions effective to allow production of viral agents. Following incubation, the viral agents so produced are collected or harvested and recovered by techniques conventional in the art. The culture conditions including cell density, multiplicity of infection, time, temperature, media, etc. are not critical and may be readily determined by the practitioner skilled in the art.

In an alternative embodiment, the cell line of the invention may be inoculated with genetically engineered baculoviruses to express foreign proteins or polypeptides of medical, pharmaceutical, or veterinary importance. As noted above, the inventions have unexpectedly found that the cell line of the invention produces substantially high yields of baculoviruses. Heterologous nucleotide sequences encoding a peptide or protein may be inserted into the baculovirus DNA, such as operably coupled or under the control of the polyhedrin promoter, so that the foreign peptide or protein is expressed upon culture of the BCIRL-HS-AM1 cell line infected with the recombinant virus. A variety of techniques have been described for the preparation of recombinant baculovirus expression vectors, particularly recombinant AcMNPV. Without being limited thereto, techniques for producing recombinant baculovirus expression vectors suitable for use with the cell line of this invention are described by Guarino et al. (U.S. Pat. Nos. 5,162,222 and 5,077,214), Page et al. (U.S. Pat. No. 5,147,788), Yamada et al. (U.S. Pat. No. 5,145,775), Fraser et al. (U.S. Pat. Nos. 5,041,379 and 4,745,051), the and Smith et al. (U.S. Pat. Nos. 4,879,236 and 4,745,051), the contents of each of which are incorporated by reference herein. Following inoculation of the cell line with the recombinant baculovirus and incubation for a sufficient time to allow expression, the foreign protein of interest may be subsequently recovered from the culture using conventional techniques.

The following example is intended only to further illustrate the invention and is not intended to limit the scope of the invention which is defined by the claims.

EXAMPLE 1

Establishment of the H. subflexa cell line

Seven female pupae of Heliothis subflexa were obtained, and under aseptic conditions were sterilized in 5% bleach and washed thoroughly in several changes of ultra pure water. The ovarian tissue was aseptically removed from the pupae in a sterile atmosphere under a vertical laminar flow hood. The excised ovarian tissue was minced with sterile scissors and treated with 0.25% trypsin for several minutes. Cells were recovered by centrifugation in a Table top centrifuge at 1500 rpm for 10 minutes. The recovered cells were suspended in 5 ml of TC199-MK culture medium [McIntosh et al., 1973, In Vitro, 8:375-378, the contents of which are incorporated by reference herein] containing 10% fetal bovine serum and the antibiotics penicillin and streptomycin, seeded into a T 25 cm$^2$ flask and incubated at 28° C. until the cells became confluent. The resultant cells were repeatedly subcultured (for one week under the same conditions) at a 1:2 split until a pure culture of the cell line of the invention was obtained. The cell line was designated BCIRL-HS-AM1.

EXAMPLE 2

Replication of Baculoviruses

The cell line obtained in Example 1 was compared with seven other Lepidopteran cell lines for their ability to grow and replicate AcMNPV as described in McIntosh [J. Invertebr. Pathol., 57: 441-442, (1991)] the contents of which are incorporated by reference herein. The other cell lines employed were *Spodoptera frugiperda* IPLB-SF21 [Vaughn et al., In Vitro 13: 213-217 (1977)], *Trichoplusia ni* TN-CL1 [McIntosh et al., In Vitro 10: 1-5 (1974)], *Plutella xylostella* BCIRL-PX2-HNU3 [Quhou et al., 1983, Journal of Central China Teachers College, Nat. Science Edition, 3:103-107], *Heliothis viriscens* BCIRL-HV-AM1 [McIntosh et al., J. Invertebr. Pathol. 37: 258-264 (1981)], *Helicoverpa zea* BCIRL-HZ-AM1, *Helicoverpa armigera* BCIRL-HA-AM1, and *Anticarsia gemmatalis* BCIRL-AG-AM.

A clone of AfMNPV, designated AfMNPVCL1 was isolated from the wild type parent by plaque purification on BCIRL-HV-AM1, and was used to inoculate cultures of all cell lines at a MOI of 0.5 (Table 1). The inoculated cells were incubated at a temperature of 28° C. for 7 days in TC199-MK media containing 10% fetal bovine serum, and penicillin and streptomycin. Viral titers (TCID$_{50}$) were assayed using TN-CL1 cells as the indicator and OB were enumerated as previously described by McIntosh et al. [1985, Intervirology 23: 150-156, and 1989, J. Invertebrate Pathology, ibid], the contents of each of which are incorporated by reference herein. OB from infected cell lines were tested for virulence using 24 hr. old larvae of *T. ni* as described by McIntosh and Ignoffo [J. Invertebr. Pathol. 37: 258-264 (1981)].

As shown in Table 1, six of the eight cell lines were susceptible to AfMNPVCL1, with BCIRL-HS-AM1 producing the highest titer of $10^{8.53}$ TCID$_{50}$/ml. Titers in the other five cell lines were lower but comparable with each other, ranging from $10^{7.08}$ TCID$_{50}$/ml for BCIRL-HV-AM1 to $10^{7.50}$ TCID$_{50}$/ml for BCIRL-PX-HNU3. AcMNPV viral titers for the same five cell lines ranged from $10^{6.40}$ to $10^{7.50}$ TCID$_{50}$/ml (McIntosh 1989, J. Invertebrate Pathology, ibid). Of the six susceptible cell lines, IPLB-SF21 was the poorest producer of OB ($2.5 \times 10^4$/ml) whereas the other five cell lines were comparable in their production of OB ($1.2-2.3 \times 10^7$/ml) as shown in Table 1. Results of the bioassays shown in Table 2 show that PIB produced by the various cell lines were infections for *T. ni* larvae.

EXAMPLE 3

Expression of foreign Genes

A recombinant AcMNPV carrying the genes for β-galactosidase and luciferase, under the control of P10 and polyhedrin promoters respectively, was obtained from Dr. C. D. Richardson, Biotechnology Research Institute, National Research Council of Canada, Montreal, Quebec. Cells of BCIRL-HS-AM1 were inoculated with the recombinant vectors and incubated in the same manner as Example 2 except the multiplicity of infection was 10. Following incubation, cultures exhibiting active luciferase and β-galactosidase were detected, indicating expression of the enzymes by infected cells.

It is understood that the foregoing detailed description is given merely by way of illustration and that modification and variations may be made therein without departing from the spirit and scope of the invention. For example, one skilled in the art will recognize that clones or mutants of the cell line of this invention may be employed to the extent that such clones or mutants retain the ability to produce viral agents, particularly of baculoviruses. In particular, clones or mutants producing at least substantially the same yield of viral agents may be employed.

TABLE 1

VIRAL AND OCCLUSION BODY PRODUCTION IN LEPIDOPTERAN CELL LINES CHALLENGED WITH A CLONAL ISOLATE (AfMNPVCL1) OF *Anagrapha falcifera* MULTIPLE NUCLEAR POLYHEDROSIS VIRUS (AfMNPV)[a]

| Cell line | Log TCID$_{50}$/ml[b] ± SE | Concentration[c] OB/ML ± SE |
|---|---|---|
| *T. ni* (TN-CL1) | 7.39 ± 0.10 | 1.2 × 10$^7$ ± 5.10 |
| *S. frugiperda* (IPLB-SF21) | 7.32 ± 0.10 | 2.5 × 10$^4$ ± 0.30 |
| *P. xylostella* (BCIRL-PX2-HNU3) | 7.50 ± 0.10 | 2.3 × 10$^7$ ± 11.20 |
| *A. gemmatalis* | 7.38 ± 0.11 | 2.2 × 10$^7$ ± 3.04 |

TABLE 1-continued

VIRAL AND OCCLUSION BODY PRODUCTION IN LEPIDOPTERAN CELL LINES CHALLENGED WITH A CLONAL ISOLATE (AfMNPVCL1) OF *Anagrapha falcifera* MULTIPLE NUCLEAR POLYHEDROSIS VIRUS (AfMNPV)[a]

| Cell line | Log $TCID_{50}/ml$[b] ± SE | Concentration[c] OB/ML ± SE |
|---|---|---|
| (BCIRL-AG-AM1) | | |
| *H. virescens* (BCIRL-HV-AM1) | 7.08 ± 0.11 | $1.6 \times 10^7$ ± 4.12 |
| *H. subflexa* (BCIRL-HS-AM1) | 8.53 ± 0.10 | $1.5 \times 10^7$ ± 7.85 |
| *H. zea* (BCIRL-HZ-AM1) | 3.93 ± 0.10 | 0 |
| *H. armigera* (BCIRL-HA-AM1) | 4.15 ± 0.11 | 0 |

[a]Cell lines were infected at a MOI of 0.5 and titered in TN-CL1 cells.
[b]Average of two determinations on duplicate flasks.
[c]Average of triplicate determinations on duplicate flasks.

TABLE 2

ACTIVITY OF OCCLUSION BODIES (OB) OF A CLONAL ISOLATE OF *Anagrapha falcifera* MULTIPLE NUCLEAR POLYHEDROSIS VIRUS (AfMNPV) in *Trichoplusia ni* LARVAE[a]

| Cell line (origin of OB) | $LC_{50}/0.1$ ml ± SE[b] |
|---|---|
| *Trichoplusia ni* (TN-CL1) | 1.8 ± 0.10 |
| *Anticarsia gemmatalis* (BCIRL-AG-AM1) | 14.3 ± 4.6 |
| *Plutella xylostella* (BCIRL-PX2-HNU3) | 4.5 ± 0.40 |
| *Heliothis subflexa* (BCIRL-HS-AM1) | 4.9 ± 1.5 |

[a]Average of four replicates; 150 larvae per test.
[b]$LC_{50}$ values were calculated after the method of R. R. Sokal and F. J. Rohlf ("Biometry," Freeman, San Francisco, 1981).

I claim:

1. A cell line *Heliothis subflexa* BCIRL-HS-AM1 and mutants thereof which are capable of producing viral agents of baculoviruses, said viral agents being selected from the group consisting of viruses, viral particles, occlusion bodies, and mixtures thereof.

2. A method for producing viral agents, wherein said viral agents are selected from the group consisting of baculoviruses, viral particles of baculoviruses, occlusion bodies of baculoviruses, and mixtures thereof, comprising the steps of:

a. inoculating cells of *Heliothis subflexa* BCIRL-HS-AM1 with baculovirus in vitro;

b. incubating to allow production of said viral agents; and c. collecting said viral agents produced in step (b).

3. The process of claim 2 wherein said viral agents are occlusion bodies of the baculovirus, and the step of collecting comprises harvesting and recovering said occlusion bodies.

4. The process of claim 2 wherein said baculovirus comprises *Autographa californica* multiple nuclear polyhedrosis virus.

5. The process of claim 4 wherein said viral agents are occlusion bodies of said *Autographa californica* multiple nuclear polyhedrosis virus and said step of collecting comprises harvesting and recovering said occlusion bodies.

6. The process of claim 2 wherein said baculovirus comprises *Anagrapha falcifera* multiple nuclear polyhedrosis virus.

7. The process of claim 6 wherein said viral agents are occlusion bodies of said *Anagrapha falcifera* multiple nuclear polyhedrosis virus and said step of collecting comprises harvesting and recovering said occlusion bodies.

* * * * *